(12) United States Patent
Parker

(10) Patent No.: US 8,142,439 B2
(45) Date of Patent: Mar. 27, 2012

(54) METHOD OF CONNECTING AN IMPACTOR TO AN ORTHOPAEDIC IMPLANT

(75) Inventor: Brad A. Parker, Warsaw, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 179 days.

(21) Appl. No.: 12/610,439

(22) Filed: Nov. 2, 2009

(65) Prior Publication Data

US 2010/0049257 A1 Feb. 25, 2010

Related U.S. Application Data

(62) Division of application No. 11/339,130, filed on Jan. 25, 2006, now Pat. No. 7,621,921.

(51) Int. Cl.
*A61B 17/56* (2006.01)
*A61F 2/34* (2006.01)
(52) U.S. Cl. .................. 606/91; 606/86 R; 606/99
(58) Field of Classification Search .............. 606/86 R, 606/91, 99
See application file for complete search history.

(56) References Cited

U.S. PATENT DOCUMENTS

| 4,632,111 A | 12/1986 | Roche |
| 5,061,270 A | 10/1991 | Aboczky |
| 5,089,003 A | 2/1992 | Fallin et al. |
| 5,169,399 A | 12/1992 | Ryland et al. |
| 5,431,657 A | 7/1995 | Rohr |
| 5,534,006 A | 7/1996 | Szabo et al. |
| 5,540,697 A | 7/1996 | Rehmann et al. |
| 5,571,200 A | 11/1996 | Cohen et al. |
| 5,584,837 A | 12/1996 | Petersen |
| 5,683,399 A | 11/1997 | Jones |
| 5,954,727 A | 9/1999 | Collazo |
| 6,110,179 A | 8/2000 | Flivik et al. |
| 6,113,605 A | 9/2000 | Storer |
| 6,205,884 B1 | 3/2001 | Foley et al. |
| 6,743,235 B2 | 6/2004 | Subba Rao |
| 7,037,311 B2 | 5/2006 | Parkinson et al. |
| 7,341,593 B2 | 3/2008 | Auxepaules et al. |
| 2003/0050645 A1 | 3/2003 | Parker et al. |
| 2004/0236337 A1 | 11/2004 | Deloge et al. |
| 2005/0038443 A1 | 2/2005 | Hedley et al. |

(Continued)

FOREIGN PATENT DOCUMENTS

| EP | 0535973 | 10/1992 |
| EP | 1570815 | 3/2005 |
| EP | 1561438 A2 | 8/2005 |

(Continued)

OTHER PUBLICATIONS

Communication dated May 17, 2011 in EP Application No. 07-001-139.0-2310 (3 pages).

(Continued)

*Primary Examiner* — Eduardo C Robert
*Assistant Examiner* — Ellen C Hammond
(74) *Attorney, Agent, or Firm* — Taylor IP, P.C.

(57) ABSTRACT

A method of connecting an impactor to an orthopaedic implant includes the steps of: providing the impactor including a shaft having a proximal end and a distal end, a trigger pivotably connected to the distal end, the trigger including a cam end, a push rod within the shaft and connected to the cam end of the trigger and a threaded pair connected to an end of the push rod opposite the trigger; providing the orthopaedic implant including a threaded hole; locating the threaded pair within the threaded hole; pivoting the trigger; linearly displacing the push rod; and radially expanding the threaded pair to engage the threaded hole.

2 Claims, 13 Drawing Sheets

U.S. PATENT DOCUMENTS

| | | |
|---|---|---|
| 2005/0131414 A1 | 6/2005 | Chana |
| 2005/0149047 A1 | 7/2005 | Parry et al. |
| 2006/0149285 A1 | 7/2006 | Burgi et al. |
| 2006/0167462 A1 | 7/2006 | Raugel et al. |
| 2007/0167952 A1 | 7/2007 | Burgi et al. |
| 2007/0270783 A1 | 11/2007 | Zumsteg et al. |
| 2008/0021481 A1 | 1/2008 | Burgi |
| 2008/0077249 A1 | 3/2008 | Gradel |

FOREIGN PATENT DOCUMENTS

| | | |
|---|---|---|
| EP | 1813229 | 1/2007 |
| WO | 0051530 A1 | 8/2000 |
| WO | 2004010882 | 2/2004 |
| WO | 2005044153 | 5/2005 |

OTHER PUBLICATIONS

European Office Action for European application No. 07 001 139.0, dated Aug. 27, 2010 (3 pages).

Communication dated Jun. 4, 2007 including European Search Report (dated May 7, 2007) and European Search Opinion of European Patent Office for application No. 07001139.0-2310 (6 pages).

Communication dated Oct. 1, 2009 of European Patent Office for application No. 07001139.0-2310 (2 pages).

Communication dated Dec. 7, 2011 from European Patent Office including European Search Report (dated Nov. 25, 2011) and opinion for European Patent Application No. EP 11 00 7915 (6 pages).

Communication dated Feb. 8, 2012 from European Patent Office for European Patent Application No. EP 07 001 139.0 - 2310 (34 pages).

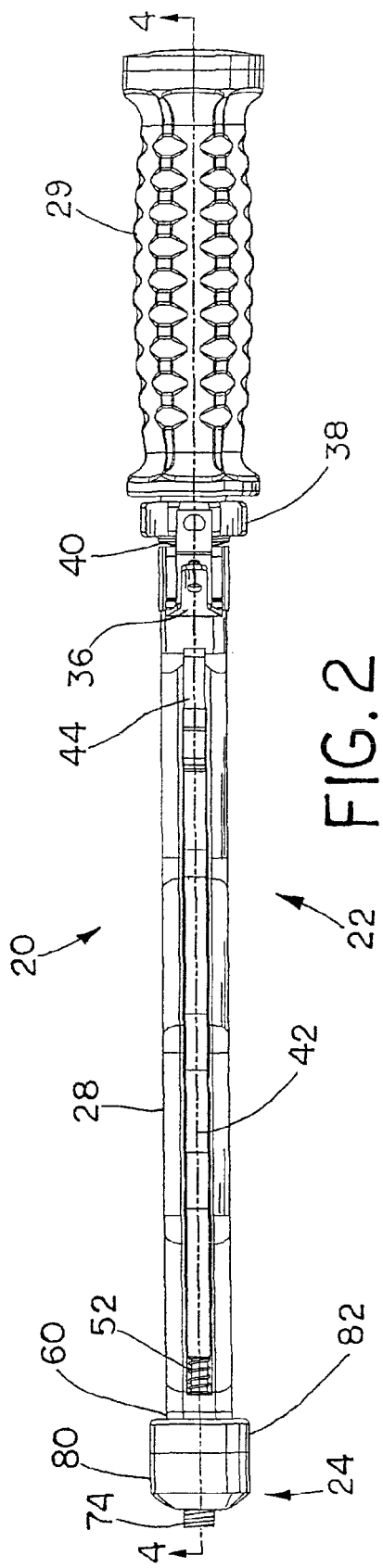
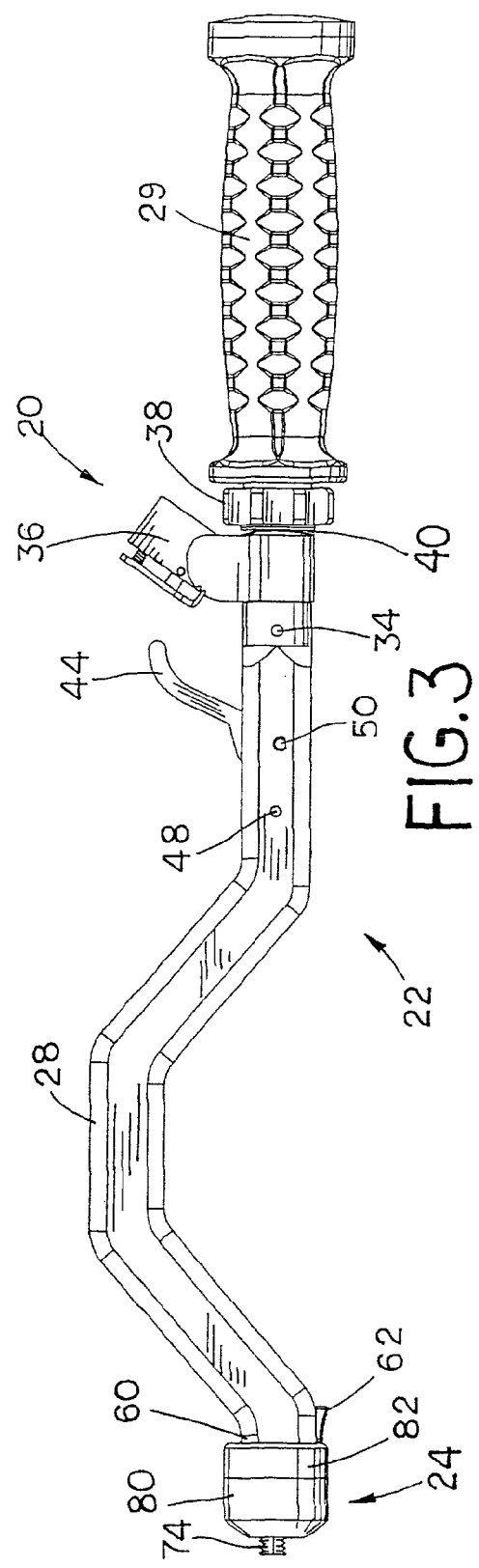

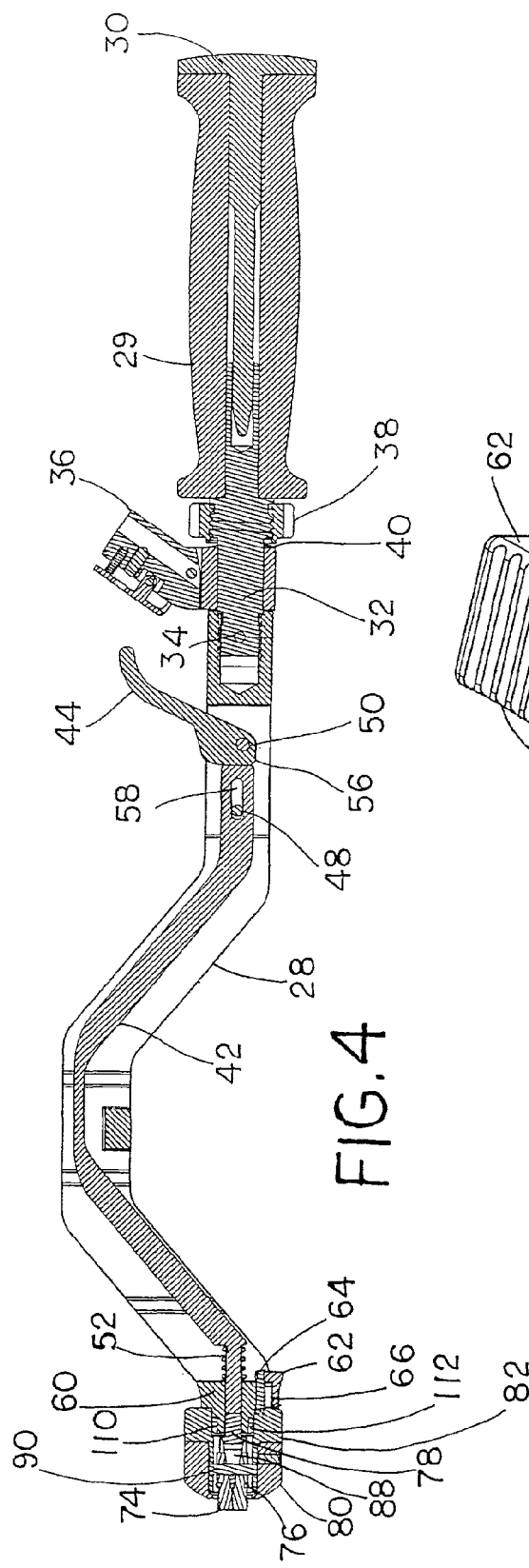
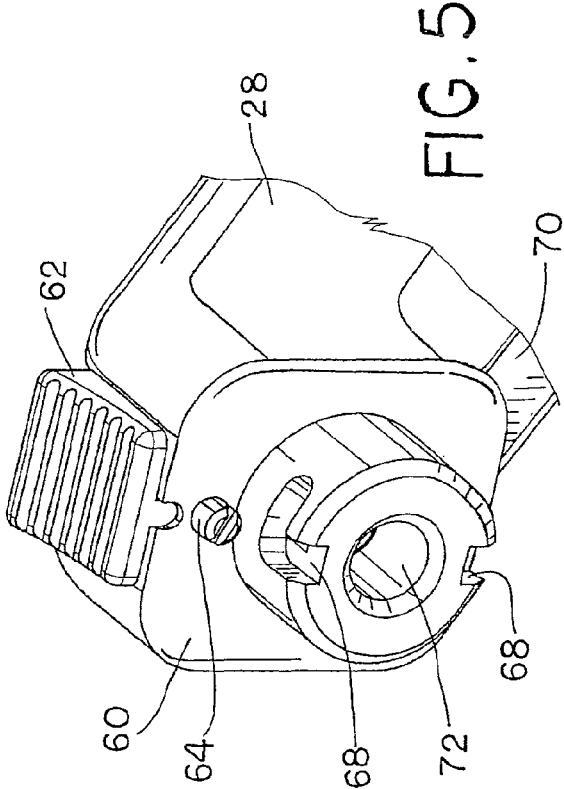

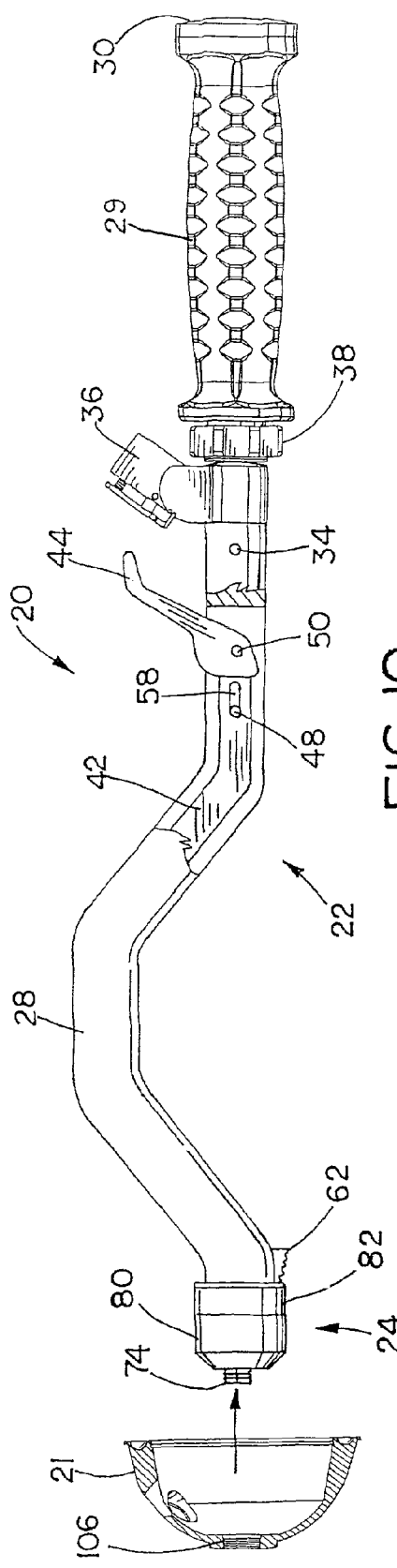
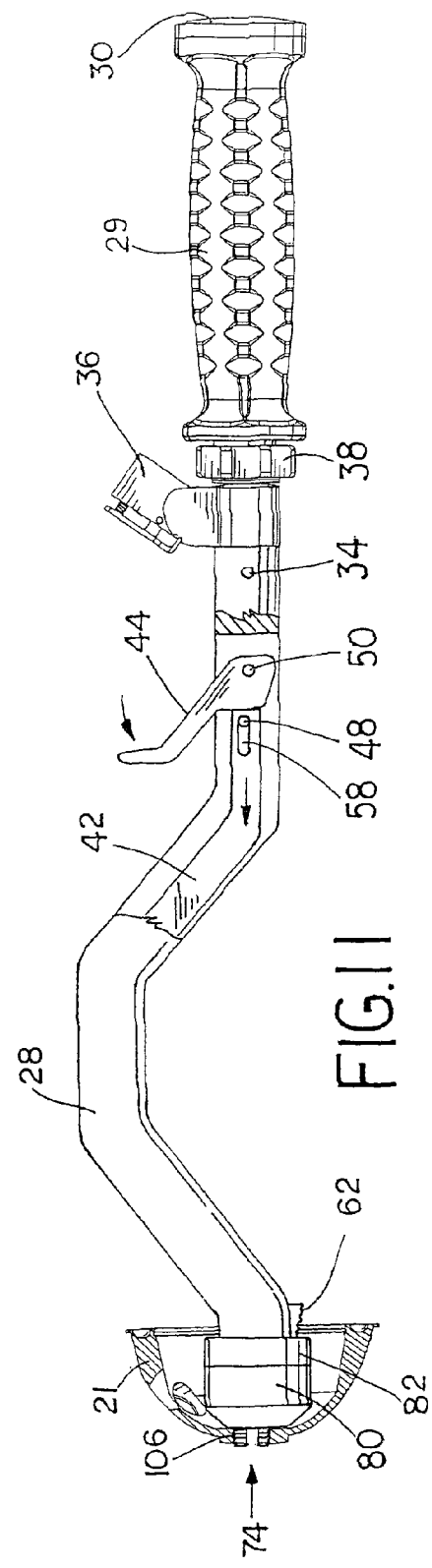

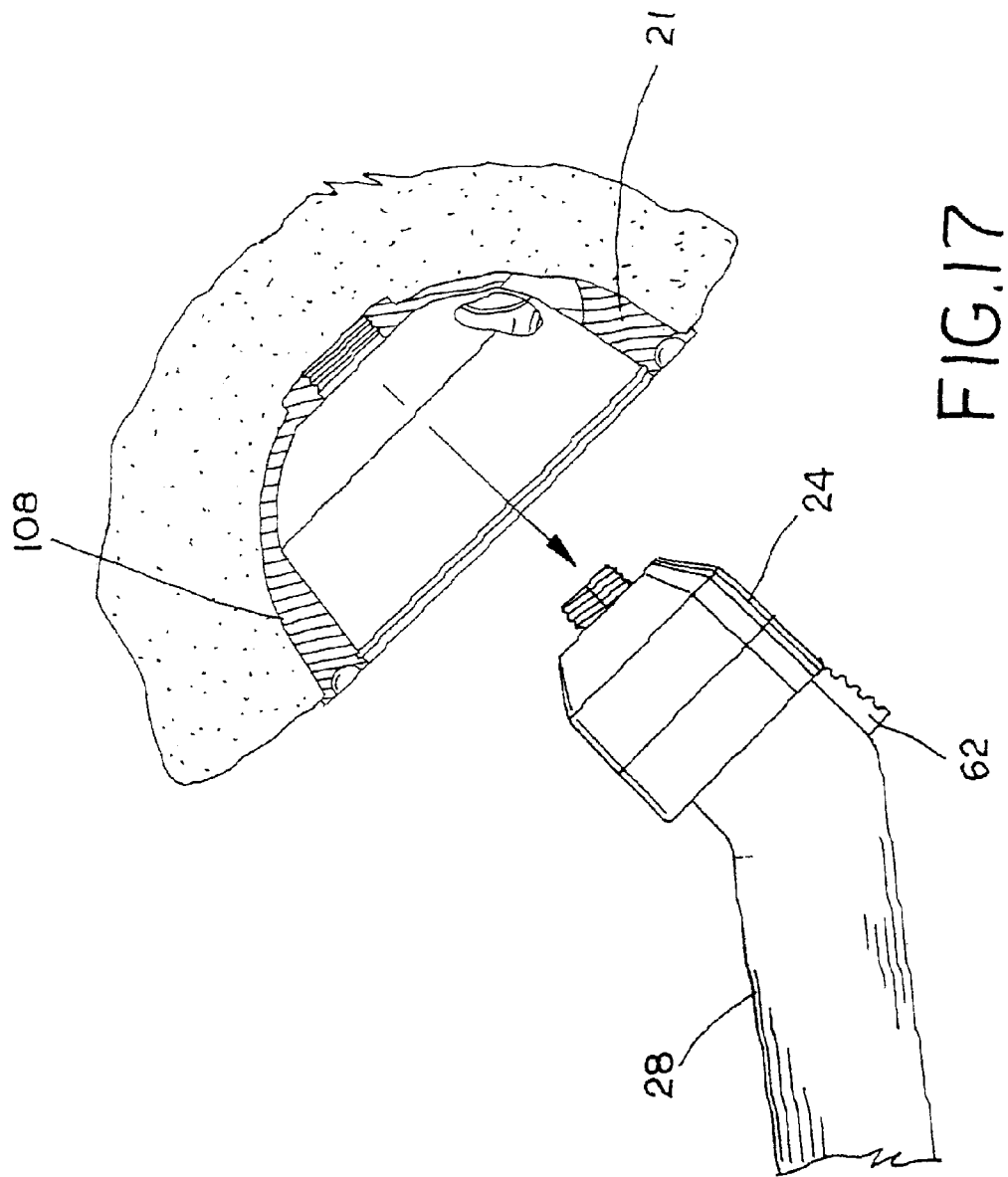

METHOD OF CONNECTING AN IMPACTOR TO AN ORTHOPAEDIC IMPLANT

CROSS REFERENCE TO RELATED APPLICATIONS

This is a division of U.S. patent application Ser. No. 11/339,130, entitled "SPLIT THREAD ORTHOPAEDIC IMPLANT IMPACTOR", filed Jan. 25, 2006, now U.S. Pat. No. 7,621,921, which is incorporated herein by reference.

BACKGROUND OF THE INVENTION

1. Field of the Invention

The present invention relates to orthopaedic instruments, and, more particularly, to orthopaedic implant impactors.

2. Description of the Related Art

The hip joint is configured as a ball and socket arrangement which includes the femoral head joined to the natural socket or acetabulum located in the pelvis. Deterioration of the acetabulum and/or femoral head can be brought about by injury or progressive diseases such as osteoarthritis. When injury or disease occurs, the damaged component(s) can be replaced or rebuilt using appropriate orthopaedic implants. In the technique known as a "total hip replacement", one method involves cementing or press-fitting an acetabular cup prosthesis into the acetabulum after the acetabulum has been sufficiently reamed to accept the cup. Additionally, fixation fasteners can be used to hold the cup in the acetabulum, and the cup can include a porous coating on the convex side to promote bone ingrowth. The femoral head can also typically be replaced.

In order to properly seat an acetabular cup into the acetabulum an impaction tool, or impactor, is used by the surgeon to firmly seat the cup. The impactor needs to securely hold the cup while the cup is being located in the acetabulum, and the impactor also needs to securely hold the cup while the cup is being impacted into the acetabulum. The acetabular cup impactor can include a surgical implement coupler which can be secured to the acetabular cup. An elongated shaft is joined to the surgical implement coupler at one end, and includes a striker cap at the opposite end of the shaft. The cup is seated in the prepared acetabulum by positioning the cup in the prepared depression, and imparting a series of blows from a mallet against the striker cap. The force of the blows is transmitted through the shaft of the impactor, to seat the cup in the prepared opening in the acetabulum. After the cup is properly seated, the surgical implement coupler of the impactor is detached from the cup.

Particularly in a minimally invasive procedure, where a small incision is made to reduce the trauma to surrounding tissue, at least two problems occur in seating an acetabular cup. It is difficult to properly align the impactor because of anatomical features that are in the way, and disconnecting the head from the cup is more difficult with limited access to the end of the tool. Cleaning and sterilization of the impactor after surgery can also be difficult.

An acetabular cup impactor is known with a curved shaft that makes proper alignment of the tool more easily accomplished during a minimally invasive surgical procedure, and includes a remotely activated surgical implement coupler for disengaging the head from an acetabular cup. The surgical implement coupler is adapted for selective attachment to and detachment from an orthopedic device such as an acetabular cup. The surgical implement coupler includes a threaded stud rotatably disposed in and retained by a sleeve. The threaded stud is adapted for threaded engagement with an acetabular cup or other orthopedic device. A universal joint or swivel drive is disposed rotatably in the shaft assembly and is drivingly connected to the threaded stud such that rotation of the swivel drive causes rotation of the threaded stud in the sleeve. A thumb wheel near the handle of the impactor actuates the swivel drive. A problem with this design is that it requires the threaded stud to be threaded into the acetabular cup, and this threading process can be tedious and time consuming, and can result in crossthreading the threaded stud into the acetabular cup with a resultant less than secure connection between the threaded stud and the acetabular cup. Another problem with this design is that it is substantially closed along the shaft which makes the internal components, such as the swivel drive, difficult to clean and sterilize.

An acetabular cup impactor or inserter is known with a curved shaft and which encloses a drive train and which includes at a far end, a prosthesis (acetabular cup, for example) engaging collet, and at the opposite end, a knob or handle which facilitates turning of the drive train by the operator. When knob is turned in one direction, the prosthesis-engaging collet locks the prosthesis against rotational movement. Further, the collet action eliminates the need of threading the acetabular prosthesis on the end of the inserter as the prosthesis can simply be placed over the collet and the collet expanded so as to grip the internal threads of the prosthesis. Turning the knob in the opposite direction can release the collet from the prosthesis. Although this design eliminates the need to thread the collet into the cup, the knob is relatively far from the impactor handle, and because of the rotational movement required by the knob, releasing the cup from the impactor is a two handed operation. Further, it is largely a closed design which makes the drive train difficult to clean and sterilize.

What is needed in the art is an orthopaedic implant impactor which is easy to use in a minimally invasive procedure, which can engage and release a prosthesis with a simple motion and which is easy to clean.

SUMMARY OF THE INVENTION

The present invention provides an orthopaedic impactor with a push rod linearly displaceable within an open shaft, where the push rod is actuated within the shaft by a trigger to engage and release an implant.

The invention comprises, in one form thereof, an orthopaedic implant impactor which includes a shaft having a proximal end and a distal end. A trigger is pivotably connected to the distal end, the trigger having a cam end. A push rod is within the shaft and is connected to the cam end of the trigger.

The invention comprises, in another form thereof, an orthopaedic implant impactor which includes a trigger having a cam end and a push rod connected to the cam end of the trigger. A shaft includes a proximal end and a distal end, and the push rod extends substantially from the proximal end to the distal end. The shaft includes an aperture exposing the push rod along a substantial length of the push rod.

The invention comprises, in another form thereof, a method of connecting an impactor to an orthopaedic implant, including the steps of: providing the impactor including a shaft having a proximal end and a distal end, a trigger pivotably connected to the distal end, the trigger including a cam end, a push rod within the shaft and connected to the cam end of the trigger, and a threaded pair connected to an end of the push rod opposite the trigger; providing the orthopaedic implant including a threaded hole; locating the threaded pair within the threaded hole; rotating the trigger; linearly displacing the push rod; and radially expanding the threaded pair to engage the threaded hole.

An advantage of the present invention is that it is easy to use in a minimally invasive surgical procedure.

Another advantage of the present invention is that it is time efficient for the surgeon to use, particularly with respect to engaging and disengaging the acetabular cup.

Yet another advantage of the present invention is that it is easy to clean and sterilize.

Yet another advantage of the present invention is that the impaction collar subassembly is easily removed from the impactor.

Yet another advantage of the present invention is that the impaction collar subassembly is easily installed onto the impactor.

Yet another advantage of the present invention is that the impaction collar subassembly can be compatible with many different manufacturer's styles of acetabular cups.

Yet another advantage of the present invention is that impactor can be easily configured for a particular manufacturer's style of acetabular cup by simply installing the appropriate impaction collar subassembly.

Yet another advantage of the present invention is that manufacturing efficiencies are achieved in that the components of the impaction collar subassembly are interchangeable, and a variety of impaction collar subassemblies can be used with a single impaction tool subassembly.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 2 is a top view of the impactor of FIG. 1;

FIG. 3 is a side view of the impactor of FIG. 1;

FIG. 4 is a cross-sectional view of the impactor of FIG. 1 taken along section line 4-4 in FIG. 2;

FIG. 5 is a fragmentary perspective end view of the impactor of FIG. 1, shown with the impaction collar subassembly removed;

FIG. 10 is a fragmentary side view of the impactor and acetabular cup of FIG. 1, shown prior to engaging the cup with the impactor;

FIG. 11 is a fragmentary side view of the impactor and acetabular cup of FIG. 1, shown after engaging the cup with the impactor;

FIG. 17 is a fragmentary cross-sectional view of the impactor/acetabular cup combination of FIG. 13, shown after setting/impacting the cup in a prepared acetabulum, and after disengaging the cup with the impactor.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
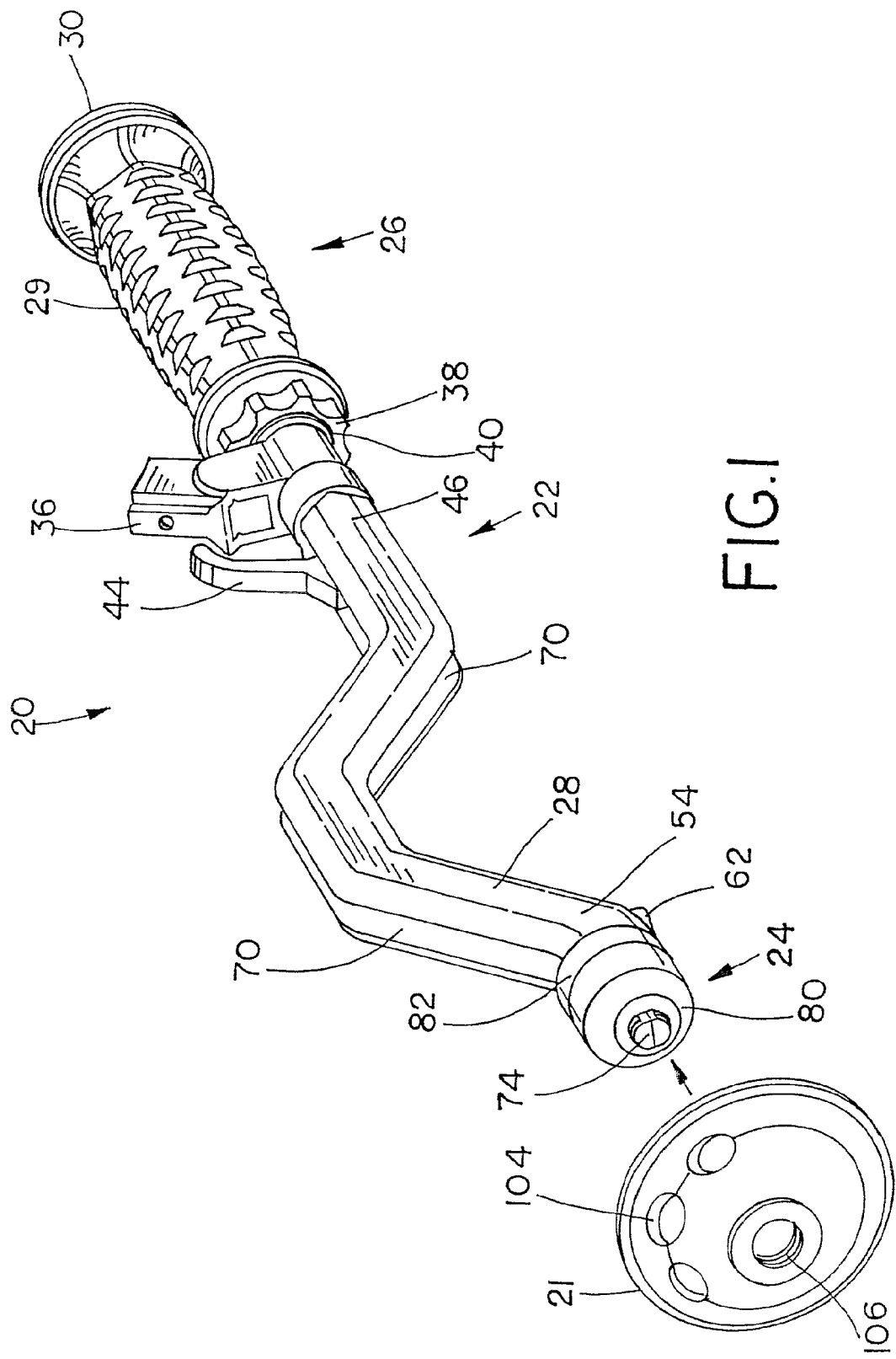
FIG. 1 is a perspective view of an embodiment of an orthopaedic implant impactor according to the present invention, shown in relation to an embodiment of a disengaged acetabular cup prosthesis.
Figure 6:
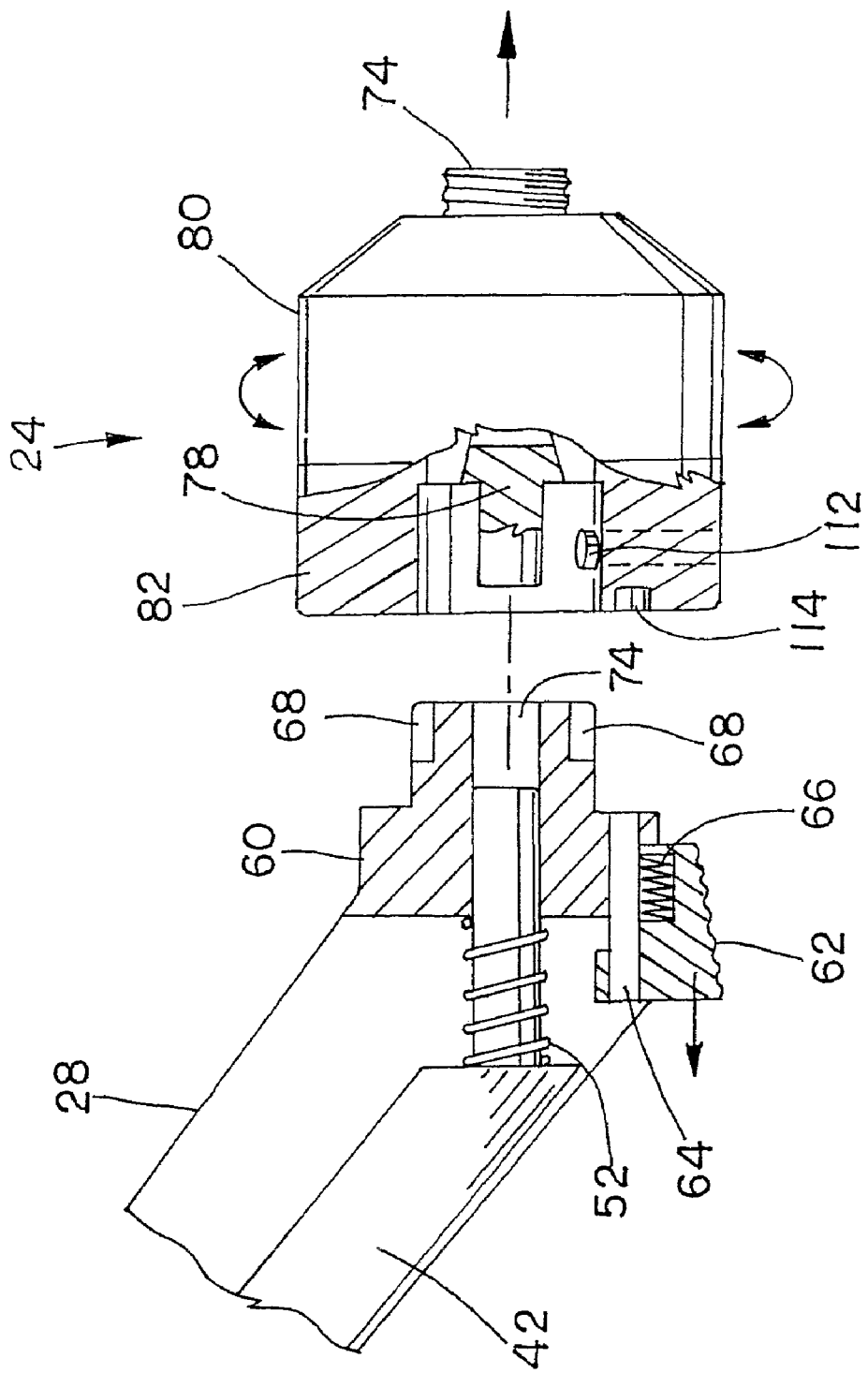
FIG. 6 is a fragmentary cross-sectional side view of the end of the impactor of FIG. 1, shown with the impaction collar subassembly prior to assembly onto the end of the impactor.

Referring now to the drawings, and more particularly to FIG. 1, there is shown an orthopaedic implant impactor 20 and an orthopaedic implant 21 shown as an acetabular cup prosthesis.

Shown more particularly in FIGS. 2-6, impactor 20 includes impaction tool subassembly 22 and impaction collar subassembly 24. Impaction tool subassembly 22 includes handle subassembly 26 connected to impactor shaft 28. Handle subassembly 26 includes a handle 29, a strikecap 30 connected to handle shaft 32, and handle shaft 32 can be fixedly connected to impactor shaft 28 using pin 34. Impaction tool subassembly 22 further includes alignment guide subassembly 36 which is rotatable around handle shaft 32, and which can be fixed in place by tightening alignment guide lock nut 38 against washer 40 and alignment guide subassembly 36. Push rod 42 and cam lock lever or trigger 44 are both connected to distal end 46 of impactor shaft 28 at pins 48 and 50, respectively. Push rod 42 is biased against trigger 44 by resilient member 52, which is shown as a spring, at proximal end 54 of impactor shaft 28. Cam lock lever 44 is pivotably connected to distal end 46 at pin 50, and includes a cam end 56 connected to push rod 42. Push rod 42 includes slot 58 which is connected to pin 48 so that push rod 42 is linearly displaceable along shaft 28 when trigger 44 is rotated. Impaction tool subassembly 22 further includes a shaft collar 60, and a release button 62 connected to a release pin 64, where both release button 62 and release pin 64 are biased toward the end of shaft collar 60 with a resilient member such as spring 66. J-slots 68, along with release button 62, release pin 64 and spring 66, facilitate a relatively easy removal and fixation of impaction collar subassembly 24 relative to impaction tool subassembly 22, as will be discussed further below. Push rod 42 extends substantially from proximal end 54 to distal end 46, and impactor shaft 28 includes at least one aperture 70 exposing push rod 42 along a substantial length of push rod 42, which allows impactor 20 to at least be easily cleaned, sterilized and maintained. Push rod 42 extends into aperture 72 of shaft collar 60.

Figure 7:
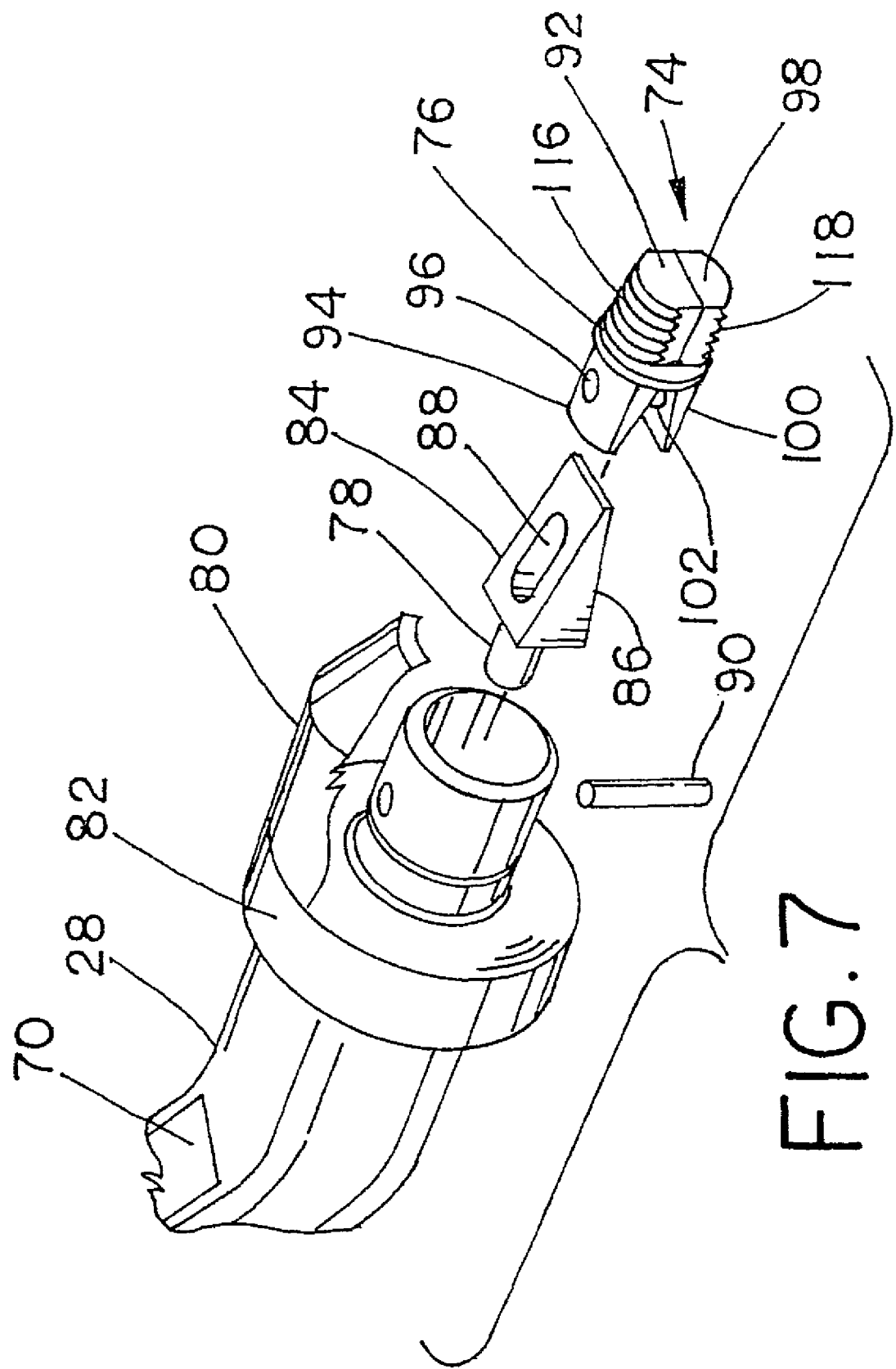
FIG. 7 is a fragmentary perspective view of the impactor of FIG. 1, shown with the impaction collar subassembly partially exploded.

Impaction collar subassembly 24 (see particularly FIGS. 4, 6 and 7) is connected to push rod 42 and shaft collar 60.

Impaction collar subassembly 24 includes a threaded pair 74 held together with an O-ring 76 and a wedge 78 inserted between threaded pair 74. Impaction collar subassembly 24 further includes a sleeve 80 and an impaction collar 82, where threaded pair 74, O-ring 76 and wedge 78 are held at least partially within impaction collar 82. Wedge 78 includes a first wedge face 84 and a second wedge face 86 and a slot 88 extending from first wedge face 84 to second wedge face 86. A pin 90 is inserted through slot 88 and connected to impaction collar 82. Threaded pair 74 includes a first half 92 with a first wedge end 94 which has a first hole 96 and a second half 98 with a second wedge end 100 which has a second hole 102, and pin 90 is also inserted through first hole 96 and second hole 102. Consequently, both wedge 78 and threaded pair 74 are constrained by pin 90 relative to impaction collar 82. That is, wedge 78 can move longitudinally, but not radially, relative to impaction collar 82; whereas each of first half 92 and second half 98 of threaded pair 74 can move radially, but not longitudinally, relative to impaction collar 82.

Figure 9:
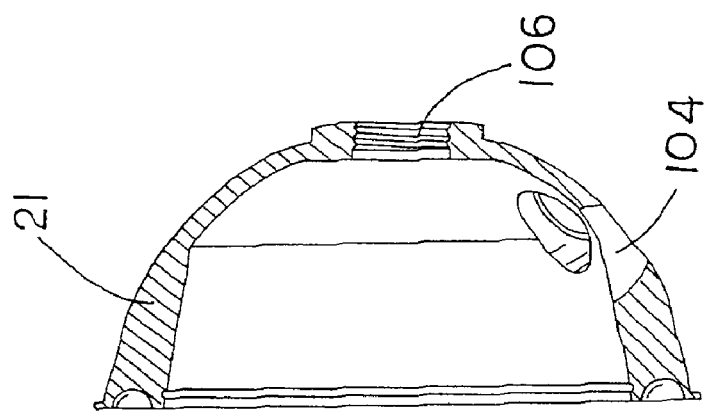
FIG. 9 is a cross-sectional view of the acetabular cup of FIG. 1 taken along section line 9-9 in FIG. 8.
Figure 8:
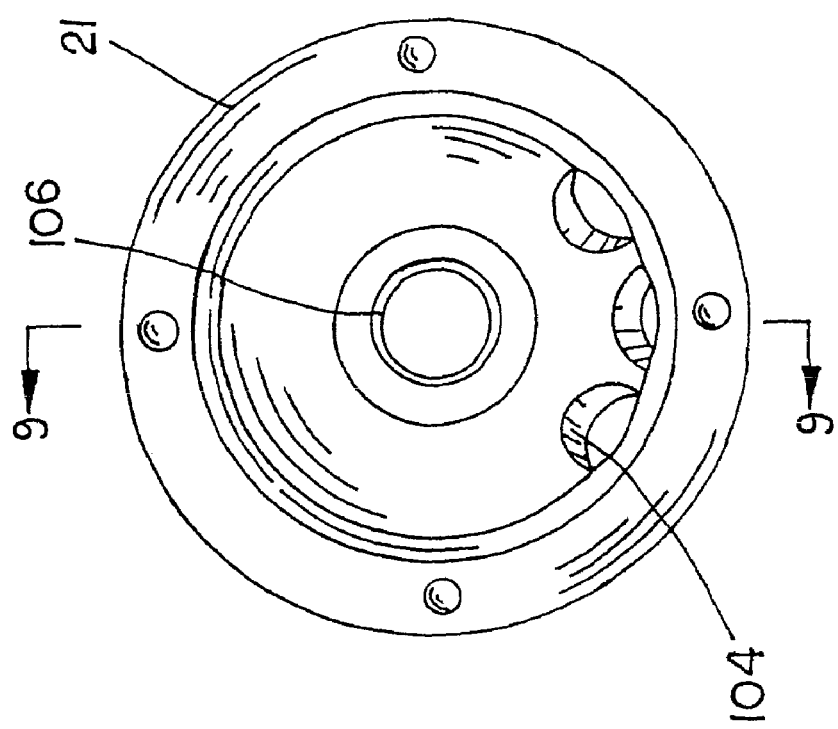
FIG. 8 is an end view of the acetabular cup prosthesis of FIG. 1.
Figure 12:
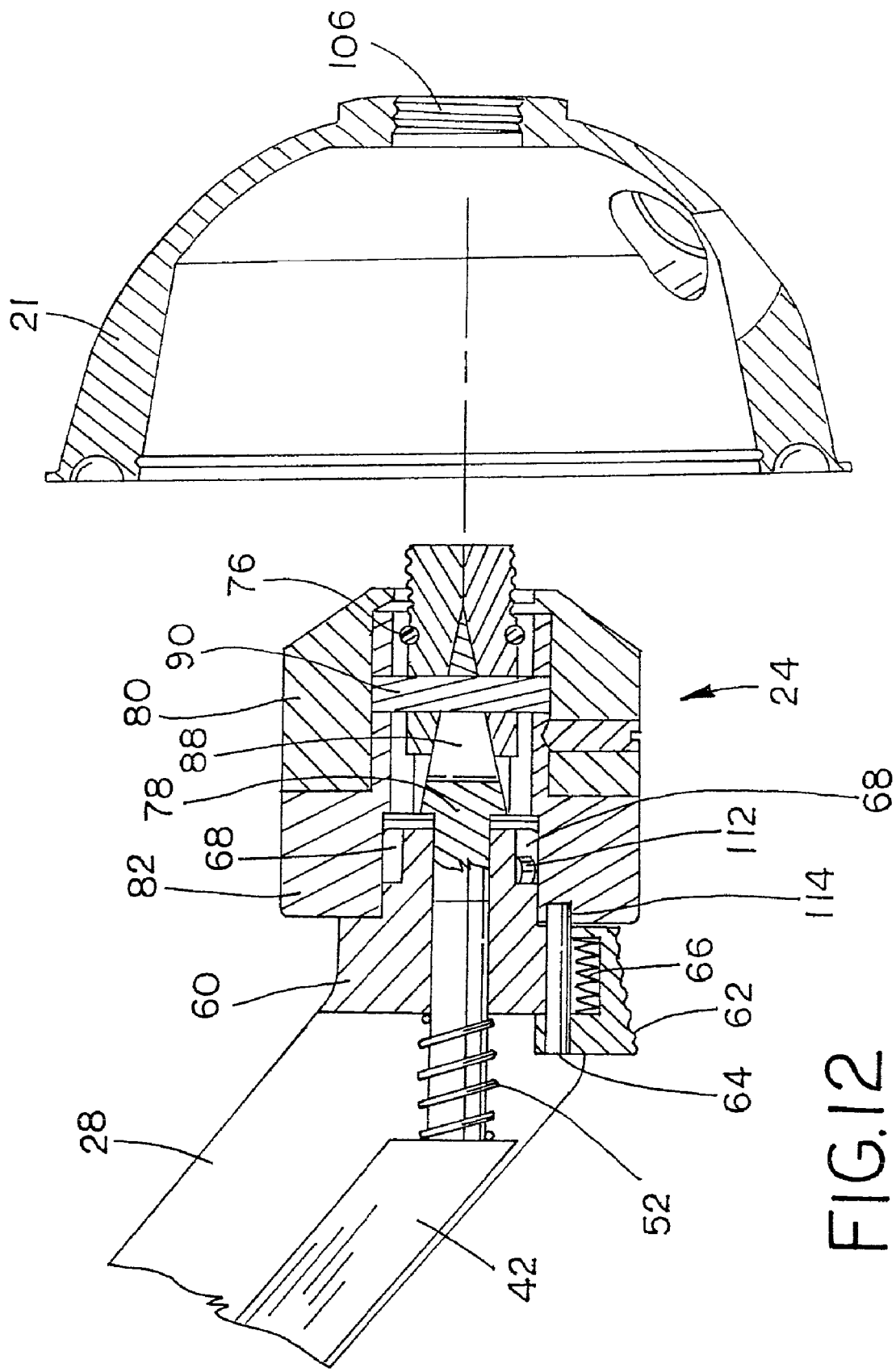
FIG. 12 is a fragmentary cross-sectional view of the impactor of FIG. 1, showing particularly the impaction subassembly connected to the end of the impaction tool subassembly, and shown prior to engaging the cup with the impactor.
Figure 13:
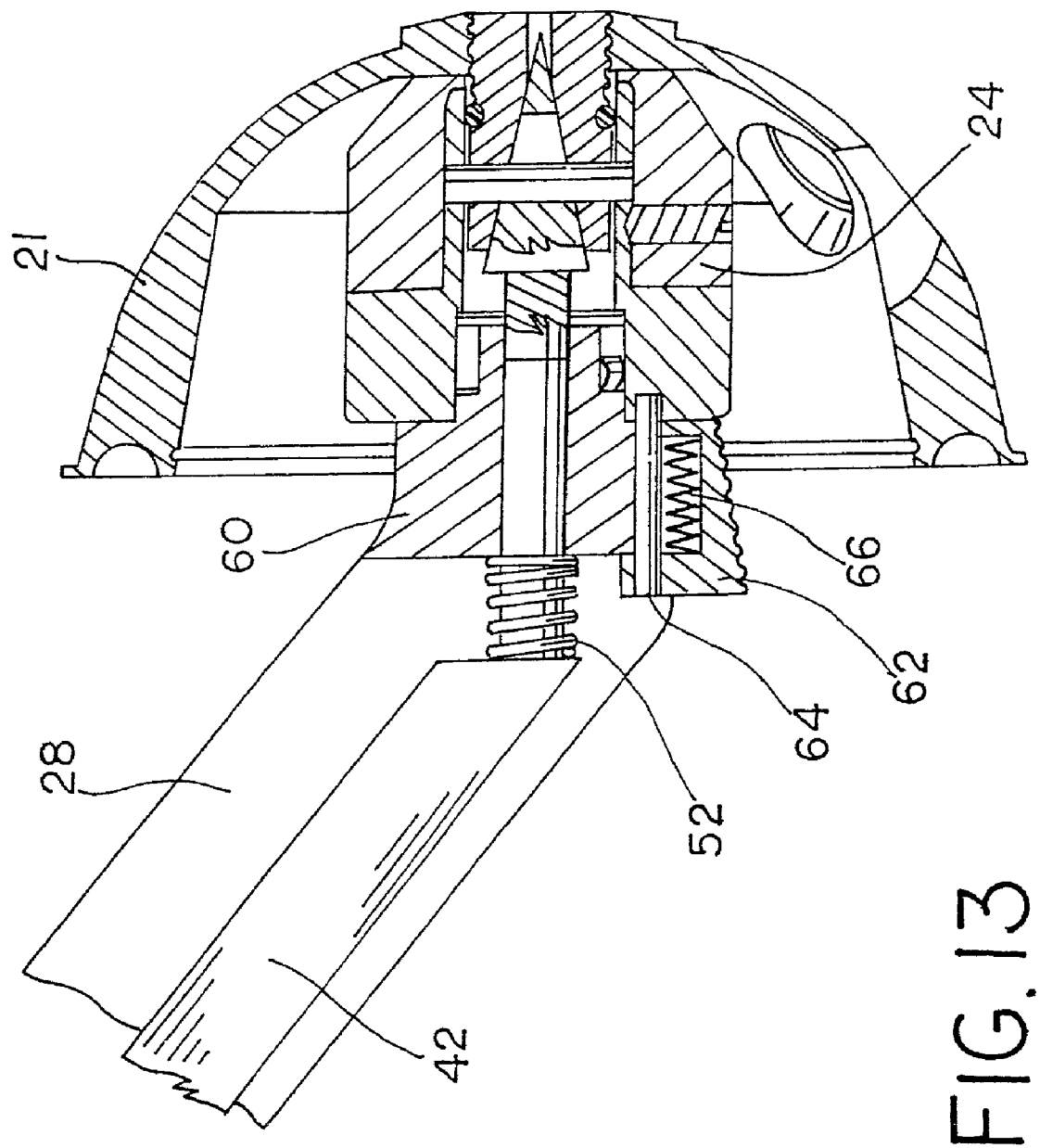
FIG. 13 is a fragmentary cross-sectional view of the impactor of FIG. 12, shown engaging the cup with the impactor.

FIGS. 8 and 9 illustrate an embodiment of acetabular cup prosthesis 21. The size and geometry of acetabular cup prosthesis 21 can vary from manufacturer to another manufacturer, and can also vary from product line to another product line of a given manufacture. The size and geometry of acetabular cup prosthesis 21 also is dictated by the patient whose hip is being replaced. Cup 21 may be porous coated on their convex side to promote bone ingrowth, and may provide some method to firmly attach a poly liner which can vary among manufacturers and/or product lines. Cup 21 can include fixation screw through holes 104 for acetabular fixation screws, and the presence, size, number and location of holes 104 can vary among manufacturers and/or product lines. Threaded hole 106, which may or may not be a through hole, is used to connect impactor 20 with implant 21. The size (for example diameter and depth) and thread type (for example threads/unit length and thread standard) of threaded hole 106 can vary among manufacturers and/or product lines and/or sizes of implant 21.

Figure 14:
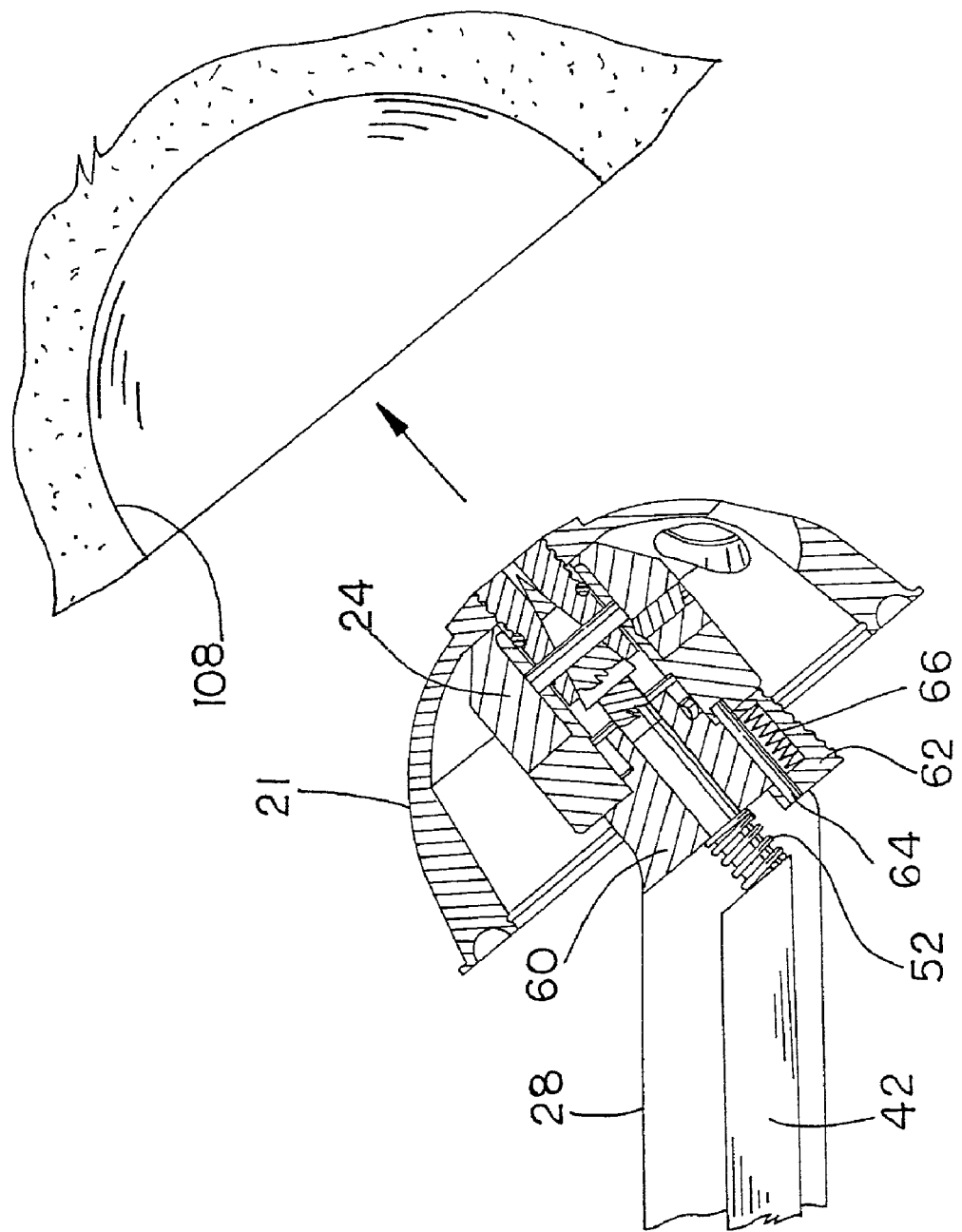
FIG. 14 is a fragmentary cross-sectional view of the impactor/acetabular cup combination of FIG. 13, shown prior to engaging the cup in a prepared acetabulum.
Figure 15:
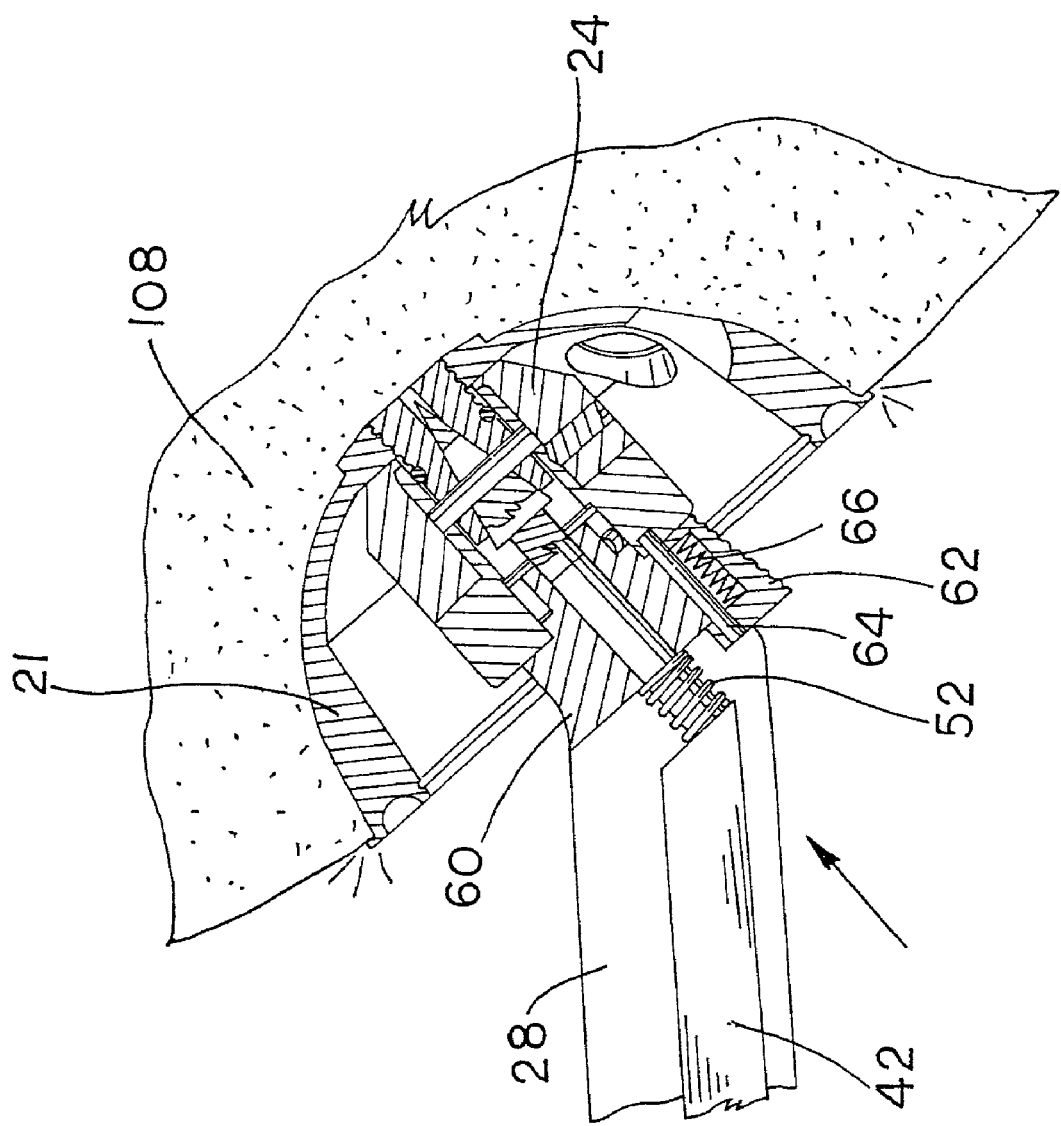
FIG. 15 is a fragmentary cross-sectional view of the impactor/acetabular cup combination of FIG. 13, shown setting the cup in a prepared acetabulum.
Figure 16:
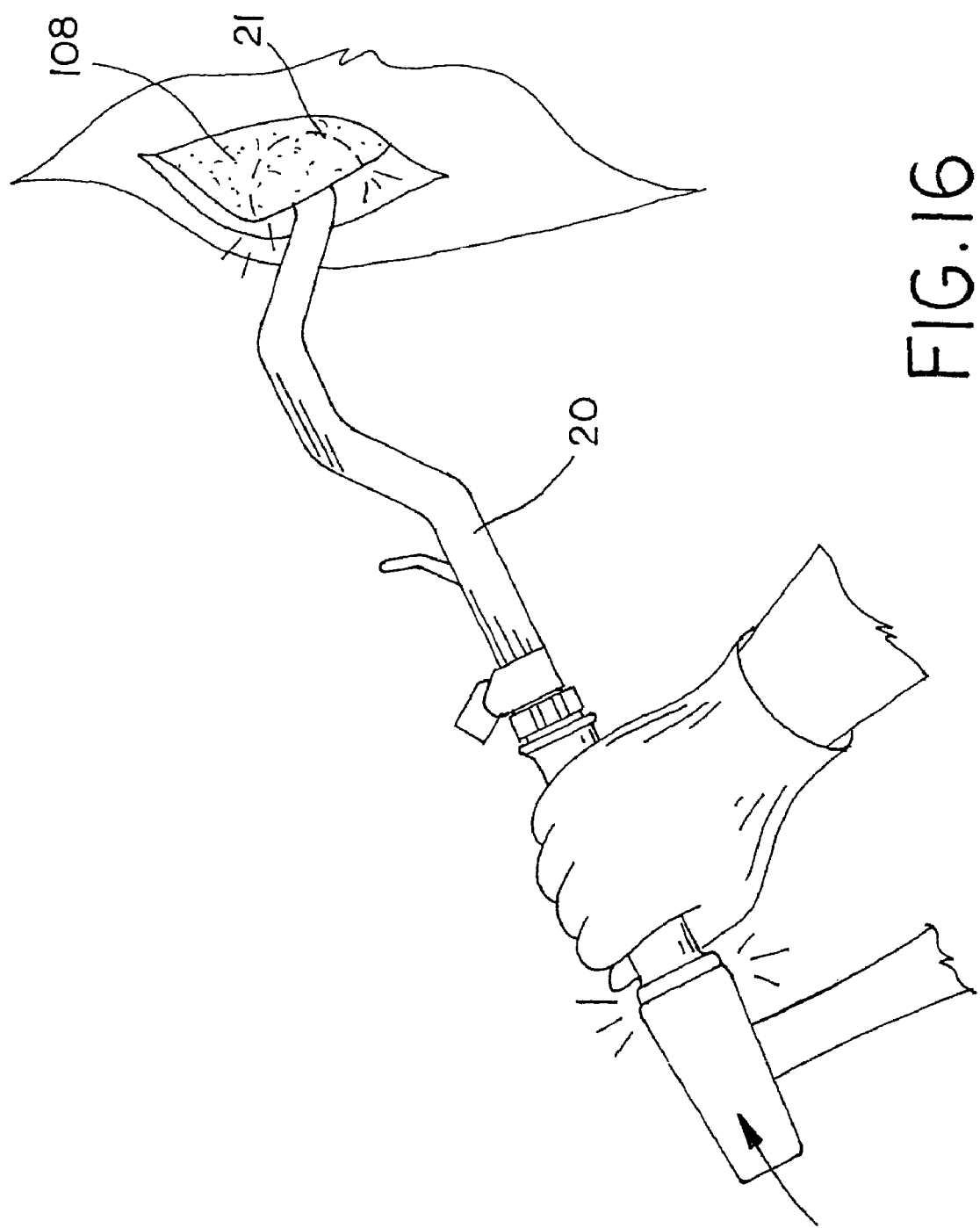
FIG. 16 is a side view of the impactor/acetabular cup combination of FIG. 13, shown impacting the cup in a prepared acetabulum.

As shown particularly in FIGS. 10-13, when cam lock lever 44 is pivoted and linearly displaces push rod 42, push rod 42 presses against wedge 78 to move wedge 78 towards the longitudinally fixed threaded pair 74, and radially expands first half 92 and second half 98 against O-ring 76. When threaded pair 74 is within threaded hole 106 of implant 21, and threaded pair 74 is actuated to radially expand within threaded hole 106, threaded pair 74 engages threaded hole 106 (FIG. 13), by engaging first threaded end 116 and second threaded end 118 into the threads of threaded hole 106, and thereby allows a surgeon to position and impact acetabular cup 21 into a prepared acetabulum 108 using impactor 20 (FIGS. 14-16). A reverse motion of trigger 44 radially retracts first half 92 and second half 98 to disengage threaded pair 74 from threaded hole 106 and thereby release impactor 20 from acetabular cup 21.

As previously discussed, the size and thread type of threaded hole 106 varies. Consequently, the size and thread type of threaded pair 74 (first threaded end 116 and second threaded end 118) can be varied to be compatible with different implants 21. Installing a different threaded pair 74 into impaction collar subassembly 24 can be tedious and time consuming, and generally not suitable for a surgical environment and/or surgical procedure. Instead, the present invention allows for quick attachment and detachment of impaction tool subassembly 22 from impaction collar subassembly 24, and a variety of impaction collar subassemblies 24 can be available, each with a different threaded pair 74 to accommodate the different threaded holes 106 (size and thread type) of different implants 21. When impaction collar subassembly 24 is slid over shaft collar 82, the base of impaction collar 82 depresses release pin 64, and locking pins 110, 112 are inserted into J-slots 68. Impaction collar subassembly 24 is then rotated relative to shaft collar 82, locking pins 110, 112 continue into J-slots 68, and release pin 64 is biased into release pin hole 114 of impaction collar subassembly 24, thereby locking impaction collar subassembly 24 relative to impaction tool subassembly 22. To release impaction collar subassembly 24 from impaction tool subassembly 22, release button 62 is depressed away from impaction collar subassembly 24, thereby releasing release pin 64 from release pin hole 114, and impaction collar subassembly 24 is rotated and then translated to release locking pins 110, 112 from J-slots 68 thereby freeing impaction collar subassembly 24 from impaction tool subassembly 22. In this way a variety of impaction collar subassemblies 24 can be available during surgery, or in a surgical tool kit, each having a different threaded pair 74 corresponding to a different type of implant 21. Once an implant 21 is selected, a corresponding impaction collar subassembly 24 can be easily and quickly installed onto impactor 20. Additionally, manufacturing efficiencies are achieved by the present invention in that the components of impaction collar subassembly 24 are interchangeable, and a variety of impaction collar subassemblies 24 can be used with a single impaction tool subassembly 22.

In use, the present invention provides a method of connecting an impactor 20 to an orthopaedic implant 21, including the steps of: providing impactor 20 including a shaft 28 having a proximal end 54 and a distal end 46, a trigger 44 pivotably connected to distal end 46, trigger 44 including a cam end 56, a push rod 42 within shaft 28 and connected to cam end 56 of trigger 44, and a threaded pair 74 connected to an end of push rod 42 opposite trigger 44; providing orthopaedic implant 21 including a threaded hole 106; locating threaded pair 74 within threaded hole 106; pivoting trigger 44; linearly displacing push rod 42; and radially expanding threaded pair 74 to engage threaded hole 106.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of connecting an impactor to an orthopaedic implant, comprising the steps of:
providing said impactor including a shaft having a proximal end and a distal end, a trigger pivotably connected to said distal end, said trigger including a cam end, a push rod within said shaft and connected to said cam end of said trigger and a threaded pair connected to an end of said push rod opposite said trigger, said threaded pair including a plurality of holes through which a coupling pin is inserted;
providing the orthopaedic implant including a threaded hole;
locating said threaded pair within said threaded hole;
pivoting said trigger;
linearly displacing said push rod; and
radially expanding said threaded pair to engage said threaded hole.

2. The method of claim 1, further comprising the step of linearly displacing a wedge by said push rod and thereby selectively moving said threaded pair between an open position and a closed position.

* * * * *